United States Patent
Paul et al.

(10) Patent No.: US 9,572,761 B2
(45) Date of Patent: Feb. 21, 2017

(54) METHOD OF TREATING HAIR

(71) Applicant: Conopco, Inc., Englewood Cliffs, NJ (US)

(72) Inventors: Prem Kumar Cheyalazhagan Paul, Spital (GB); Susan Pye, Wirral (GB); Brian Douglas Wall, Wirral (GB)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 14/400,988

(22) PCT Filed: May 15, 2013

(86) PCT No.: PCT/EP2013/060022
§ 371 (c)(1),
(2) Date: Nov. 13, 2014

(87) PCT Pub. No.: WO2013/174690
PCT Pub. Date: Nov. 28, 2013

(65) Prior Publication Data
US 2015/0328119 A1    Nov. 19, 2015

(30) Foreign Application Priority Data
May 21, 2012   (EP) .................................... 12168632

(51) Int. Cl.
*A61Q 5/04* (2006.01)
*A61K 8/60* (2006.01)
*A45D 7/06* (2006.01)
*A61K 8/365* (2006.01)

(52) U.S. Cl.
CPC . *A61K 8/60* (2013.01); *A45D 7/06* (2013.01); *A61K 8/365* (2013.01); *A61K 8/602* (2013.01); *A61Q 5/04* (2013.01)

(58) Field of Classification Search
None
See application file for complete search history.

(56) References Cited

U.S. PATENT DOCUMENTS

| | | | |
|---|---|---|---|
| 3,025,218 A | 3/1962 | Strain | |
| 4,349,537 A | 9/1982 | Forbriger, Jr. | |
| 4,409,204 A | 10/1983 | Lang | |
| 5,002,761 A | 3/1991 | Mueller et al. | |
| 6,517,822 B1 | 2/2003 | Buck | |
| 6,723,308 B2 | 4/2004 | Browning | |
| 8,192,730 B2 * | 6/2012 | Elliott | A61K 8/60 424/70.1 |
| 2007/0298003 A1* | 12/2007 | Chandra | A61K 8/60 424/70.12 |
| 2008/0019939 A1 | 1/2008 | Verboom | |
| 2010/0300471 A1* | 12/2010 | Malle | A61K 8/362 132/204 |

FOREIGN PATENT DOCUMENTS

| | | |
|---|---|---|
| EP | 1393708 | 3/2004 |
| WO | WO03039497 | 5/2003 |
| WO | WO03039497 A1 | 5/2003 |
| WO | WO2005025524 | 3/2005 |
| WO | WO2005025524 A1 | 3/2005 |
| WO | WO2005084622 | 9/2005 |
| WO | WO2005084623 | 9/2005 |
| WO | WO2009047251 | 4/2009 |
| WO | WO2009138288 | 11/2009 |
| WO | WO2009138288 A1 | 11/2009 |
| WO | WO2010001632 | 1/2010 |
| WO | WO2010049434 | 5/2010 |
| WO | WO2010049434 A2 | 5/2010 |
| WO | WO2010141098 | 12/2010 |
| WO | WO2012084532 | 6/2012 |
| WO | WO2013174575 | 11/2013 |
| WO | WO2013174575 A1 | 11/2013 |

OTHER PUBLICATIONS

IPRP2 in PCTEP2013060022 (April) dated Apr. 28, 2014; p. 1 to p. 11.
IPRP2 in PCTEP2013060022 (May) dated May 16, 2014; p. 12 to p. 21.
Search Report EP13157663 dated Aug. 28, 2013; p. 22 to p. 23.
Search Report in EP12168631 dated Oct. 11, 2012; p. 24 to p. 25.
Search Report in EP12168632 dated Oct. 12, 2012; p. 26 to p. 27
Search Report in PCTEP2013057809 dated Jul. 17, 2013; p. 28 to p. 31.
Search Report in PCTEP2013060022 dated Jul. 17, 2013; p. 32 to p. 35.
Written Opinion EP13157663 dated Aug. 28, 2013; p. 36 to p. 36.
Written Opinion in EP12168631 dated Oct. 11, 2012; p. 37 to p. 39.
Written Opinion in EP12168632 dated Oct. 12, 2012; p. 40 to p. 42.
Written Opinion in PCTEP2013057809 dated Jul. 17, 2013; p. 43 to p. 49.
Written Opinion in PCTEP2013060022 dated Jul. 17, 2013; p. 50 to p. 54.
IPRP2 in PCTEP2013060022 (April) dated Apr. 28, 2014.
IPRP2 in PCTEP2013060022 (May) dated May 16, 2014.
Search Report EP13157663 dated Aug. 28, 2013.
Search Report in EP12168631 dated Oct. 11, 2012.
Search Report in EP12168632 dated Oct. 12, 2012.
Search Report in PCTEP2013057809 dated Jul. 17, 2013.
Search Report in PCTEP2013060022 dated Jul. 17, 2013.
Written Opinion EP13157663 dated Aug. 28, 2013.

(Continued)

*Primary Examiner* — Jyothsna Venkat
(74) *Attorney, Agent, or Firm* — Greenberg Traurig, LLP

(57) ABSTRACT

The present invention is directed to a method for straightening hair, wherein the method of straightening hair comprises the step of: (1) applying to the hair a hair treatment composition comprising: i) gluconolactone, in which the level of gluconolactone is from 1.5 to 5 wt % of the total hair treatment composition; and ii) citric acid, in which the level of citric acid is from 1 to 5 wt % of the total hair treatment composition; and (2) applying heat to the hair at a temperature of greater than 120° C. for at least 10 seconds after the hair treatment composition is applied to the hair, wherein the hair treatment composition is applied to dry hair.

5 Claims, No Drawings

(56) References Cited

OTHER PUBLICATIONS

Written Opinion in EP12168631 dated Oct. 11, 2012.
Written Opinion in EP12168632 dated Oct. 12, 2012.
Written Opinion in PCTEP2013057809 dated Jul. 17, 2013.
Written Opinion in PCTEP2013060022 dated Jul. 17, 2013.

\* cited by examiner

METHOD OF TREATING HAIR

The invention relates to a method of hair straightening.

The current hair market has a wide range of straightening products. A common way to retain a particular hairstyle is by application of a hairspray, mousses, gel, lotions or wax. The materials in these compositions are generally film forming agents, resins, gums, and/or adhesive polymers. Such methods do not straighten the hair from wash to wash.

Permanent hair straightening compositions that are on the market are based on chemical treatment of the hair in a two-step process using thiol- or hydroxide-based reducing agents followed by a neutralisation or oxidation step. Such systems have various negatives associated with them; in that the process itself is difficult to conduct, in many instances this straightening process is undertaken by a qualified hairdresser in a professional salon. Furthermore the straightening process damages the hair, has an unpleasant odour and can cause irritation to the scalp.

WO2005/084623 discloses styling/straightening compositions containing gluconolactone; however hair styled in this manner does not retain its style after subsequent washing The present invention has now found that hair can be straightened in a way that mitigates damage, yet remains straight even after subsequent washing.

SUMMARY OF INVENTION

The present invention relates to a method of straightening the hair comprising the step of applying to the hair a hair treatment composition comprising:
i) at least 0.8 wt % of the total composition of a sugar lactone; and
ii) at least 0.8 wt % of the total composition of a bidentate or tridentate carboxylic acid in which the ratio of sugar lactone to acid is 1:5 to 5:1; and
iii) heating the resulting composition to a temperature of greater than 120° C. for at least 10 seconds.

DESCRIPTION OF INVENTION

The composition of the invention comprise a sugar lactone, preferably the sugar lactone is a monosaccharide, more preferably gluconolactone, especially preferred is glucono-delta-lactone.

The level of sugar lactone, preferably gluconolactone is at least 0.8 wt % of the total composition, preferably less than 8.0 wt %. More preferably the level of sugar lactone is from 1.0 wt % to 6.0 wt % of the total composition, most preferably the level of sugar lactone is from 1.5 to 5.0 wt %.

Compositions of the invention comprise a bidentate or tridentate organic acids. Preferably the organic acid is a di or tri carboxylic acid, more preferably the carboxylic acid is a short chain (C2-C10, preferably C3 to C6)) carboxylic acids, especially preferred are di or tri acid carboxylic acid, citric acid being particularly preferred.

The bi or tridentate carboxylic acid is present in the total composition at a level of at least 0.8 wt %, more preferably at al level greater than 0.9 wt %, most preferably at a level from 1.0 to 5.0 wt %.

The ratio of sugar lactone to bi.tridentate carboxylic acid is from 1:5 to 5:1, more preferably from 1:3 to 3:1.

Hair care compositions of the present invention can comprise a carrier, or a mixture of such carriers, which are suitable for application to the hair. The carriers are present at from about 0.5% to about 99.5%, preferably from about 5.0% to about 99.5%, more preferably from about 10.0% to about 96.0%, of the composition. As used herein, the phrase "suitable for application to hair" means that the carrier does not damage or negatively affect the aesthetics of hair or cause irritation to the underlying skin.

Compositions according to the invention comprise a buffer or pH adjuster. Preferred buffers or pH adjusters include weak acids and bases such glycine/sodium hydroxide, lactic acid, succinic acid, acetic salt and salts thereof. Frequently a mixture of buffering system. Preferably the pH is 4 or below; more preferably between 2.5 and 3.5.

Compositions according to the invention are preferably aqueous compositions intended to be applied to the hair after shampooing and rinsing. They are massaged into preferably dry hair and, heating, preferably followed by further rinsing with water prior to drying the hair. By aqueous composition, it is meant that the compositions of the invention comprise 60% by weight or more of water, preferably 70% or more, more preferably 80% or more.

When the hair care composition is a hair spray, tonic, gel, or mousse the preferred solvents include water, ethanol, volatile silicone derivatives, and mixtures thereof. The solvents used in such mixtures may be miscible or immiscible with each other. Mousses and aerosol hair sprays can also utilise any of the conventional propellants to deliver the material as a foam (in the case of a mousse) or as a fine, uniform spray (in the case of an aerosol hair spray). Examples of suitable propellants include materials such as trichlorofluoromethane, dichlorodifluoromethane, difluoroethane, dimethylether, propane, n-butane or isobutane. A tonic or hair spray product having a low viscosity may also utilise an emulsifying agent. Examples of suitable emulsifying agents include nonionic, cationic, anionic surfactants, or mixtures thereof. If such an emulsifying agent is used, it is preferably present at a level of from about 0.01% to about 7.5% by weight based on total weight of the composition. The level of propellant can be adjusted as desired but is generally from about 3% to about 30% by weight based on total weight for mousse compositions and from about 15% to about 50% by weight based on total weight for aerosol hair spray compositions.

Hair styling creams or gels also typically contain a structurant or thickener, typically in an amount of from 0.01% to 10% by weight of the total composition.

Suitable spray containers are well known in the art and include conventional, non-aerosol pump sprays i.e., "atomisers", aerosol containers or cans having propellant, as described above, and also pump aerosol containers utilising compressed air as the propellant.

The formulation may include conditioning materials such as surfactants, cationic conditioners suitable for hair, quaternary silicone polymers, silicone based conditioners and their emulsions, and amino functional silicones and their emulsions.

Further general ingredients suitable for all product forms include, sun-screening agents, anti-dandruff actives, carboxylic acid polymer thickeners and emulsifiers for emulsifying the various carrier components of the compositions of the invention.

In some aspects of this invention it is highly desirable if the composition comprises a styling aid.

Particularly useful as styling aids with this invention are hair styling polymers. Hair styling polymers are well known articles of commerce and many such polymers are available commercially which contain moieties which render the polymers cationic, anionic, amphoteric or nonionic in nature. The polymers may be synthetic or naturally derived.

The amount of the hair styling polymer may range from 0.1 to 10%, preferably 0.5 to 8%, more preferably 0.75 to 6% by weight based on total weight of the composition.

The compositions of the present invention may also contain adjuncts suitable for hair care. Generally such ingredients are included individually at a level of up to 2, preferably up to 1 wt % of the total composition. Suitable hair care adjuncts, include amino acids, sugars and ceramides.

Although the product may be in any form suitable for application to the hair it is preferable if it is a rinse off product. Products used to condition the hair are especially preferred.

In use the composition of the invention is applied to the hair and then preferably rinsed off up to 60 minutes after application, more preferably this product is rinsed off 40 minutes after application.

The method of the invention comprises applying compositions of the invention followed by a heating step. The hair should be heated to a temperature above 120° C., more preferably above 150° C., most preferably above 170° C. It is preferable if the maximum temperature applied to the hair is 220° C.

The following non-limiting Examples further illustrate the preferred embodiments of the invention. All percentages referred to in the examples and throughout this specification are by weight based on total weight unless otherwise indicated.

EXAMPLES

Experiment 1

Dark brown European wavy#6 switches of length 25 cm and weight 2 gms, were dosed with 1 ml each of 2% citric acid; 4% citric acid; 2% gluconolactone; 4% gluconolactone and (2% citric acid+2% gluconolactone) solutions. They were left to dry at 20° C. and 50% RH for at least 30 minutes. When dry the switches were straightened 7 times with irons (set at 180° C.) and exposed to high humidity (30° C. 80% RH) for an hour. The volume of the switches at the end of the hour shows the straightening benefit of the sugars (volume refers to the projection of the switch image on to the screen and is given in $mm^2$).

| Treatment | Volume ($mm^2$) | % Benefit |
|---|---|---|
| water | 13617 | 0.0 |
| 2% Gluconolactone | 11020 | 19.1 |
| 2% Citric acid | 12017 | 11.8 |
| 4% Gluconolactone | 8700 | 36.1 |
| 4% Citric acid | 11948 | 12.3 |
| 2% Citric acid + 2% Glucoconolactone | 6989 | 48.7 |

From the table it can be seen that the combination gives synergistic benefits compared to the benefits expected from single actives alone i.e. the % benefit of combination is far greater than the sum of the % benefit of the individual actives at 2% level. The combination benefit is also greater than the single actives at the 4% level.

Experiment 2

Dark brown European wavy#6 switches of length 25 cm and weight 2 gms, were dosed with 1 ml each of solutions, the compositions of which are given in table below. They were left to dry at 20° C. and 50% RH for at least 30 minutes. When dry the switches were straightened 7 times with irons (set at 180° C.) and exposed to high humidity (30° C. 80% RH) for 1 hour. The volume of the switches shows the straightening benefit of the sugars (volume refers to the projection of the switch image on to the screen and is given in $mm^2$).

| Treatment | Volume (($mm^2$) | % benefit |
|---|---|---|
| 0% Citric acid + 2% Gluconolactone | 11020 | 0.00 |
| 0.1% Citric acid + 2% Gluconolactone | 11822 | −7.28 |
| 0.5% Citric acid + 2% Gluconolactone | 11174 | −1.40 |
| 1% Citric acid + 2% Gluconolactone | 8406 | 23.72 |
| 2% Citric acid + 2% Gluconolactone | 6989 | 36.57 |

From the table it is clear that adding small amounts of citric acid to gluconolactone does not provide any benefits over gluconolactone alone.

Experiment 3

Switches were treated with 1 gm of the combination of aqueous solution of 2% Citric acid+2% Gluconolactone solution or 4% Citric acid solution or 4% Gluconolactone solution. They were dried for at least 30 minutes and ironed straight with 180° C. irons. They were subsequently washed twice with shampoo and conditioner. After the second wash the switches with the combination showed better straightness, more volume down and greater length of switches compared to the single active treated switches. The combination switches retained the original straight style created with the initial application better than the single active treated switches.

The invention claimed is:

1. A method for straightening hair, wherein the method of straightening hair comprises the step of:
   (1) applying to the hair a hair treatment composition consisting of:
      i) gluconolactone, in which the level of gluconolactone is from 1.5 to 5 wt % of the total hair treatment composition; and
      ii) citric acid, in which the level of citric acid is from 1 to 5 wt % of the total hair treatment composition; and
   (2) applying heat to the hair at a temperature of greater than 120° C. for at least 10 seconds after the hair treatment composition is applied to the hair, wherein the hair treatment composition is applied to dry hair.

2. The method according to claim 1 in which the pH of the hair treatment composition is 4 or below at 20° C.

3. The method according to claim 1 in which the heat is applied to the hair at a temperature above 150° C.

4. The method of straightening the hair according to claim 1 in which the hair treatment composition is not washed off between application of the hair treatment composition and the heating process.

5. The method according to claim 4 in which the hair treatment composition is left on the hair for a minimum of 10 minutes before application of heat.

* * * * *